US010441466B2

(12) United States Patent
Han et al.

(10) Patent No.: US 10,441,466 B2
(45) Date of Patent: Oct. 15, 2019

(54) GOGGLES

(71) Applicant: BOARDRIDERS IP HOLDINGS, LLC, Huntington Beach, CA (US)

(72) Inventors: Seung Yun Han, Seoul (KR); Kyung Sub Lim, Seoul (KR)

(73) Assignee: BOARDRIDERS IP HOLDINGS, LLC, Huntington Beach, CA (US)

( * ) Notice: Subject to any disclaimer, the term of this patent is extended or adjusted under 35 U.S.C. 154(b) by 125 days.

(21) Appl. No.: 15/036,224

(22) PCT Filed: Dec. 5, 2013

(86) PCT No.: PCT/KR2013/011220
§ 371 (c)(1),
(2) Date: May 12, 2016

(87) PCT Pub. No.: WO2015/083851
PCT Pub. Date: Jun. 11, 2015

(65) Prior Publication Data
US 2016/0287444 A1 Oct. 6, 2016

(30) Foreign Application Priority Data
Dec. 4, 2013 (KR) ........................ 10-2013-0150119

(51) Int. Cl.
*A61F 9/02* (2006.01)
*A61F 9/06* (2006.01)

(52) U.S. Cl.
CPC .............. *A61F 9/025* (2013.01); *A61F 9/061* (2013.01)

(58) Field of Classification Search
CPC ........... A61F 9/061; A61F 9/045; A61F 9/025
(Continued)

(56) References Cited

U.S. PATENT DOCUMENTS 3,593,338 A * 7/1971 Penny .................... A42B 3/225
2/427
8,366,267 B2 * 2/2013 Lin .......................... G02C 1/04
351/153

(Continued)

FOREIGN PATENT DOCUMENTS

| KR | 10-2011-0083001 A | 7/2011 |
|---|---|---|
| KR | 20-2012-0003775 U | 6/2012 |
| KR | 10-1258637 B1 | 5/2013 |

*Primary Examiner* — Alissa J Tompkins
*Assistant Examiner* — Cameron A Carter
(74) *Attorney, Agent, or Firm* — Nixon & Vanderhye P.C.

(57) ABSTRACT

Disclosed are goggles. The goggles are provided so that they comprise: a main body unit worn on the face of a user; a lens unit that is coupled to the main body unit and has a fastening protrusion formed to protrude toward the main body unit; and a fastening unit that has a fastening recess formed therein and is coupled to the main body to lock and unlock the fastening protrusion, wherein the fastening unit includes a body part movably coupled to the main body unit and a guide protrusion for guiding the moving direction of the body part, the main body unit has a guide hole formed at a position corresponding to the guide protrusion, the guide protrusion being received in the guide hole, and the fastening unit further included a protrusion part coupled to the body part to push the fastening protrusion outward such that the lens unit is separated from the main body unit when the fastening protrusion is unlocked according to the movement of the body part into the main body unit.

7 Claims, 3 Drawing Sheets

(58) Field of Classification Search
USPC .................................... 2/431, 426, 427, 445
See application file for complete search history.

(56) References Cited

U.S. PATENT DOCUMENTS

| | | | | |
|---|---|---|---|---|
| 2004/0083540 | A1* | 5/2004 | Dondero | A61F 9/025 2/436 |
| 2007/0277297 | A1* | 12/2007 | Chiang | A63B 33/002 2/426 |
| 2008/0155736 | A1* | 7/2008 | Paulson | A61F 9/025 2/441 |
| 2009/0038057 | A1* | 2/2009 | Tews | A42B 3/223 2/424 |
| 2009/0038059 | A1* | 2/2009 | McNeal | A61F 9/025 2/439 |
| 2009/0313746 | A1* | 12/2009 | Wang | A61F 9/025 2/431 |
| 2010/0132703 | A1* | 6/2010 | Ivory | A42B 3/26 128/201.24 |
| 2011/0007262 | A1* | 1/2011 | Taylor | G02C 1/04 351/60 |
| 2012/0255104 | A1* | 10/2012 | Didier | A61F 9/025 2/426 |
| 2013/0097855 | A1* | 4/2013 | Li | A61F 9/025 29/700 |
| 2013/0104300 | A1* | 5/2013 | Park | A61F 9/025 2/439 |
| 2013/0185849 | A1* | 7/2013 | Laughlin | A61F 9/025 2/431 |
| 2015/0143619 | A1* | 5/2015 | Cross | A63B 33/002 2/427 |

* cited by examiner

[Fig. 1]
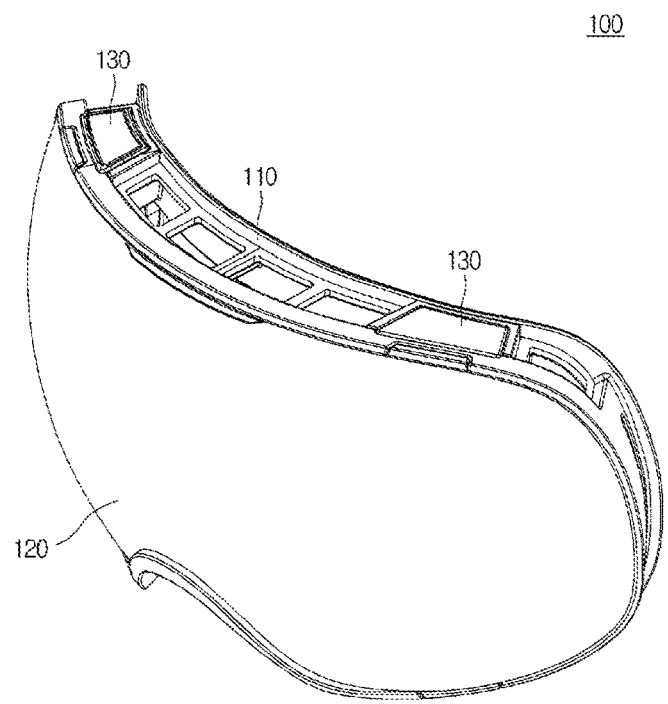
[Fig. 2]
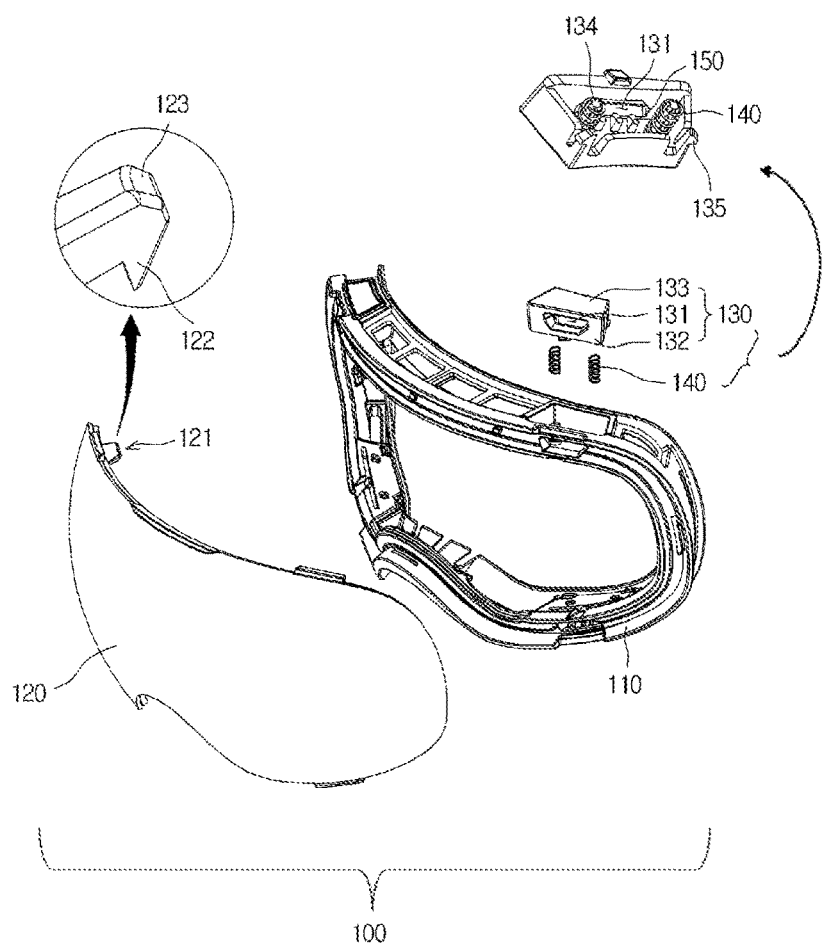

[Fig. 3]
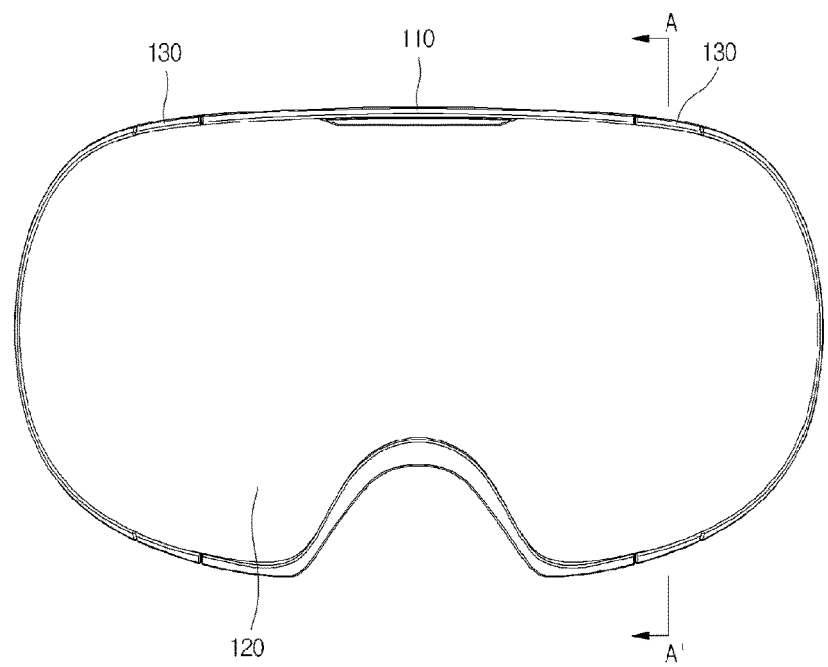
[Fig. 4]
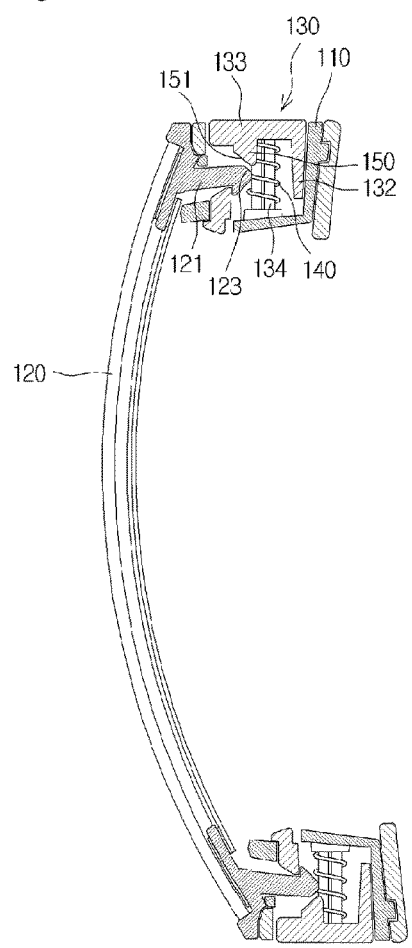

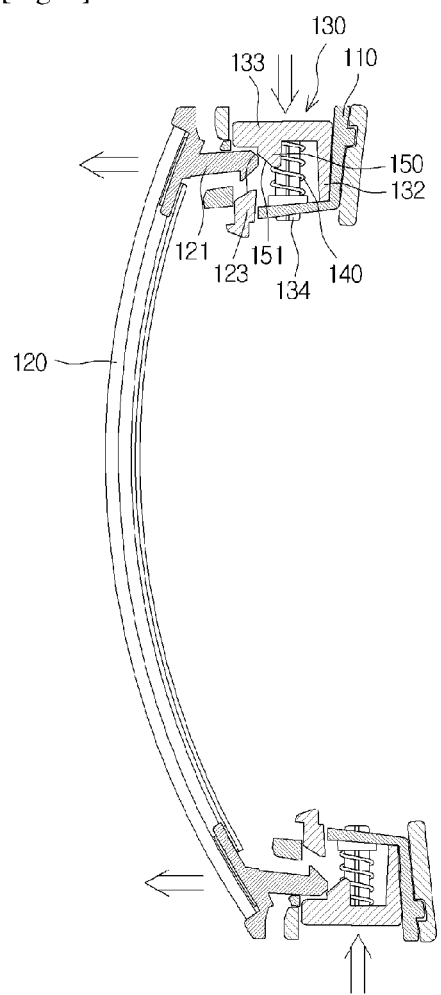
[Fig. 5]

GOGGLES

This application is the U.S. national phase of International Application No. PCT/KR2013/011220 filed 5 Dec. 2013, which designated the U.S. and claims priority to KR Patent Application No. 10-2013-0150119 filed 4 Dec. 2013.

TECHNICAL FIELD

The present invention relates to goggles.

BACKGROUND ART

Goggles are safety glasses for protecting eyes from dust and strong light and may be used for leisure activities such as climbing or skiing or may be used in daily activities such as driving a motorcycle.

Particularly, since people enjoy winter sports such as skiing and snowboarding at a slope of a mountain area covered with snow at a low temperature with a strong wind, it is necessary to protect eyes from the strong wind and a snowstorm while enjoying winter sports described above. Also, since snow reflects sunlight with a high reflectance, it is necessary to protect eyes from strong sunlight. Accordingly, goggles may be an essential apparatus for people who enjoy winter sports described above.

Recently, a large number of goggles with high level functionality have been developed. Korean Patent Publication No. 10-2011-0083001 (Jul. 20, 2011) discloses one of the related art of the present invention.

DISCLOSURE

Technical Problem

An aspect of the present invention is to provide goggles with a detachable lens.

Technical Solution

One aspect of the present invention provides goggles including a body unit worn on a face of a user, a lens unit coupled with the body unit and including a fastening protrusion which protrudes toward the body unit, and a fastening unit which includes a fastening groove to be engaged with the fastening protrusion and is coupled with the body unit to restrict or release the fastening protrusion. Here, the fastening unit includes a body portion movably coupled with the body unit and a guide protrusion configured to guide a movement direction of the body portion. The body unit includes a guide hole formed at a position corresponding to the guide protrusion so that the guide protrusion is accommodated therein. The fastening unit further includes a protruding portion coupled to the body portion and configured to push the fastening protrusion outward so that the lens unit is separated from the body unit when the fastening protrusion is released according to a movement of the body portion into the body unit.

The protruding portion may protrude toward an inside of the body unit so that an end of the protruding portion pushes out an end of the fastening protrusion.

A first inclined plane may be formed at a part of the fastening protrusion in contact with the protruding portion.

A second inclined plane facing the first inclined plane may be formed at a part of the protruding portion in contact with the fastening protrusion.

Advantageous Effects

According to one embodiment of the present invention, a lens of goggles is easily detachable from a body.

BRIEF DESCRIPTION OF DRAWINGS

FIG. 1 is a perspective view of goggles according to one embodiment of the present invention.

FIG. 2 is an exploded perspective view of the goggles according to one embodiment of the present invention.

FIG. 3 is a front view of the goggles according to one embodiment of the present invention.

FIG. 4 is a cross-sectional view illustrating a lens unit of the goggles according to one embodiment of the present invention engaged with a body unit, taken along line A-A' shown in FIG. 3.

FIG. 5 is a cross-sectional view illustrating the lens unit of the goggles according to one embodiment of the present invention released from the body unit, taken along line A-A' shown in FIG. 3.

MODE FOR INVENTION

Hereinafter, goggles according to embodiments of the present invention will be described in detail with reference to the attached drawings, in which like reference numerals designate like elements and repetitive explanations thereof will be omitted.

Also, the terms used hereafter such as first, second, etc. are merely identifying symbols for distinguishing identical or corresponding elements and the identical or corresponding elements are not be limited to the terms such as first, second, etc.

Also, coupling not only refers to a physically direct contact between respective elements but also refers to a concept including a case in which one element is disposed between two elements and each of the two elements is in contact with the one element.

FIG. 1 is a perspective view of goggles according to one embodiment of the present invention, FIG. 2 is an exploded perspective view of the goggles according to one embodiment of the present invention, FIG. 3 is a front view of the goggles according to one embodiment of the present invention, FIG. 4 is a cross-sectional view illustrating a lens unit of the goggles according to one embodiment of the present invention engaged with a body unit, taken along line A-A' shown in FIG. 3, and FIG. 5 is a cross-sectional view illustrating the lens unit of the goggles according to one embodiment of the present invention released from the body unit, taken along line A-A' shown in FIG. 3.

Referring to FIGS. 1 to 3, goggles 100 according to one embodiment of the present invention may include a body unit 110, a lens unit 120, and a fastening unit 130. The body unit 110 may include a fastening protrusion 121. The fastening unit 130 may include a fastening groove 131, a body portion 132, and a guide protrusion 134, and may further include a protruding portion 150.

The body unit 110 is a portion to be worn on a face of a user and may be formed with a curve to correspond to a shape of the face of the user. The body unit 110 may be formed of a material with a light weight and strong durability and may be formed of a synthetic resin material.

The lens unit 120 may be mounted on the body unit 110 and may include the fastening protrusion 121 for being mounted on the body unit 110.

The lens unit 120 may be formed of a transparent material or may be formed of a material which is opaque when viewed from the outside but is transparent when viewed from the inside.

The fastening unit 130 may be coupled with the body unit 110 to allow the lens unit 120 to be coupled with the body unit 110. In this case, the fastening unit 130 may include the fastening groove 131 to be engaged and coupled with the fastening protrusion 121 formed on the lens unit 120.

The fastening unit 130 may be movably coupled with the body unit 110. The fastening unit 130 is vertically movable with respect to the body unit 110. As the fastening unit 130 moves along the body unit 110, the fastening protrusion 121 may be engaged with or released from the fastening groove 131. Due thereto, it is possible to control to attach or detach the lens unit 120 to or from the body unit 110.

The fastening protrusion 121 formed on the lens unit 120 may protrude toward the body unit 110, the fastening groove 131 may be open toward the lens unit 120, and the fastening groove 131 may be formed at a position corresponding to the fastening protrusion 121 to fasten the fastening protrusion 121 to the fastening groove 131.

The fastening unit 130 may include the body portion 132, a pressurizing portion 133, and the guide protrusion 134 and may further include the protruding portion 150. Also, the body unit 110 may include a guide hole 111 in which the guide protrusion 134 is accommodated.

The body portion 132 may be movably coupled with the body unit 110. The pressurizing portion 133 may be formed on a top surface of the body portion 132.

The pressurizing portion 133 may transfer a pressure to move the body portion 132. The pressurizing portion 133 may have a flat panel shape and may have an area capable of being pushed by a finger tip of the user. An emblem, logo, etc. for identifying a product may be attached to the pressurizing portion 133.

The guide protrusion 134 may be coupled with the body portion 132 and may guide a movement direction when the body portion 132 moves. The guide protrusion 134 may have a bar shape.

The guide hole 111 in which the guide protrusion 134 is accommodated may be formed in the body unit 110 to which the fastening unit 130 is coupled. The guide protrusion 134 and the guide hole 111 may guide the movement direction of the body portion 132.

The guide hole 111 may have the same cross section as that of the guide protrusion 134. When the guide protrusion 134 has the bar shape, the guide hole 111 may have a circular shape. Due to the guide protrusion 134 and the guide hole 111, the body portion 132 may not deviate and may linearly move.

An elastic member 140 may be formed at the guide protrusion 134. When the fastening unit 130 moves into the body unit 110, the elastic member 140 may provide an elastic force which moves the fastening unit 130 outside the body unit 110 to allow the fastening unit 130 to automatically return to an original state thereof.

The elastic member 140 may be a spring, and the spring may be formed on an outer circumferential surface of the guide protrusion 134. According to the goggles 100 further including the elastic member 140, when the fastening unit 130 moves into the body unit 110, since the fastening unit 130 may return without additional force provided, it may be easy to attach or detach the lens unit 120 to or from the body unit 110.

The protruding portion 150 may be formed on the body portion 132 and may push the fastening protrusion 121 outward to separate the lens unit 120 from the body unit 110. As shown in FIG. 2, a plurality of such protruding portions 150 may be formed on an inner side of the pressurizing portion 133.

When to separate the lens unit 120 from the body unit 110, the user pressurizes the fastening unit 130 to move into the body unit 110 and the protruding portion 150 becomes in contact with the fastening protrusion 121. The protruding portion 150 may push the fastening protrusion 121 outward, thereby separating the lens unit 120 from the body unit 110.

A plurality of such fastening units 130 may be formed. In this case, the fastening units 130 may be formed along an outer perimeter of the body unit 110 and may be disposed being spaced apart from each other. The plurality of fastening units 130 may be formed at four corners of the goggles 100. In this case, the user may pressurize the fastening unit 130 using four fingers. Each of the fastening units 130 may have the protruding portion 150, and in this case, the lens unit 120 may be more easily separated.

Hereinafter, referring to FIGS. 4 and 5, the fastening and releasing of the lens unit 120 will be described.

Referring to FIG. 4, when the lens unit 120 moves toward the body unit 110 while being separated from the body unit 110, the fastening protrusion 121 is inserted into the fastening groove 131. When the fastening unit 130 moves outside the body unit 110 while the fastening protrusion 121 is inserted in the fastening groove 131, the fastening protrusion 121 may be restricted by the fastening groove 131. Accordingly, the fastening protrusion 121 and the fastening groove 131 are fastened, and thus the lens unit 120 may be restricted by the body unit 110.

A holding portion 122 may be formed at an end of the fastening protrusion 121. The holding portion 122 may allow the fastening protrusion 121 to be engaged and coupled with the fastening groove 131. When the fastening protrusion 121 is inserted in the fastening groove 131, the fastening protrusion 121 may not depart from the fastening groove 131 due to the holding portion 122. By the fastening protrusion 121 including the holding portion 122, cohesion between the fastening protrusion 121 and the fastening groove 131 may be increased.

The fastening unit 130 may include a stopper 135 not to be separated from the body unit 110 after being coupled with the body unit 110. The stopper 135 may be formed to protrude from a side of the fastening unit 130 and a plurality of such stoppers 135 may be formed. An accommodating groove which accommodates the stopper 135 may be formed at the body unit 110.

Referring to FIG. 5, when the user applies a force to the pressurizing portion 133 while the lens unit 120 is restricted by the body unit 110, the body portion 132 moves into the body unit 110. When the body portion 132 moves, the guide protrusion 134 may be inserted into the guide hole 111.

In this case, as described above, the protruding portion 150 pushes out the fastening protrusion 121, and thus the lens unit 120 may be separated from the body unit 110.

As shown in FIG. 5, the protruding portion 150 may protrude into the body unit 110 and an end of the protruding portion 150 may push out the end of the fastening protrusion 121.

By the protruding portion 150, the lens unit 120 may be automatically separated from the body unit 110 due to a linear movement of the fastening unit 130. That is, it may become notably easy to separate the lens unit 120 from the body unit 110.

Movement directions of the body portion 132 and the protruding portion 150 may be perpendicular to a direction in which the lens unit 120 is pushed and moved.

A first inclined plane 123 may be formed at the fastening protrusion 121. The first inclined plane 123 may be formed at a part of the fastening protrusion 121 in contact with the protruding portion 150. The first inclined plane 123 may be formed to be inclined toward the body unit 110 from the lens unit 120. In this case, as shown in FIG. 5, the movement direction of the protruding portion 150 and a direction in which the fastening protrusion 121 is pushed and moved may become perpendicular to each other.

A second inclined plane 151 may be formed at a part of the protruding portion 150 in contact with the fastening protrusion 121. The second inclined plane 151 may face the first inclined plane 123. That is, as shown in FIG. 4, the second inclined plane 151 and the first inclined plane 123 may be formed to overlap each other. Since the second inclined plane 151 pushes out the first inclined plane 123 of the fastening protrusion 121 and a contact area therebetween increases, the fastening protrusion 121 may be prevented from being damaged.

Meanwhile, the body unit 110 of the goggles 100 according to one embodiment of the present invention may include a plurality of body frames. For example, the body unit 110 may include a first body frame and a second body frame. The first body frame and the second body frame may form a space portion in the body unit 110, in which the fastening unit 130 is accommodated.

By the body unit 110 including the first body frame and the second body frame, since the first body frame and the second body frame can mutually absorb shocks when the goggles 100 is shocked, durability of the goggles 100 may be improved.

The lens unit 120 of the goggles 100 according to one embodiment of the present invention may include a lens frame and a plurality of lenses and adhesive frames.

The lens frame may be coupled with edges of the lenses to protect the lenses. Also, the lens frame may include the fastening protrusion 121 to allow the lens unit 120 to be coupled with the body unit 110. The lenses may be attached to both sides of the lens frame, and the adhesive frames may be disposed between the lens frame and the lenses.

As described above, according to the goggles 100 according to one embodiment of the present invention, it is easy to attach or detach the lens unit 120 to or from the body unit 110 in the goggles 100. Particularly, by the protruding portion 150, it may become notably easy to separate the lens unit 120 from the body unit 110.

When it is easy to attach or detach the lens unit 120, the user may selectively wear various lenses according to user's preference and may use lenses adequate for surroundings. Also, when a defect occurs in a lens, since the goggles 100 may be repaired only by replacing the lens unit 120, a maintenance cost may be reduced.

Although one embodiment of the present invention has been shown and described, it would be appreciated by those skilled in the art that changes may be made in this embodiment by adding, changing, omitting, or supplementing elements without departing from the principles and spirit of the present invention, the scope of which is defined in the claims and their equivalents.

DESCRIPTION OF REFERENCE NUMERALS

100: Goggles
110: Body unit
111: Guide hole
120: Lens unit
121: Fastening protrusion
122: Holding portion
123: First inclined plane
130: Fastening unit
131: Fastening groove
132: Body portion
133: Pressurizing portion
134: Guide protrusion
135: Stopper
140: Elastic member
150: Protruding portion
151: Second inclined plane

The invention claimed is:

1. Goggles comprising:
a body unit configured to be worn on a face of a user;
a lens unit detachably coupled with the body unit and comprising a fastening protrusion which protrudes toward the body unit; and
a fastening unit which comprises a fastening groove to accommodate the fastening protrusion and is coupled with the body unit to lock or release the fastening protrusion, wherein
the fastening protrusion comprises a holding portion protruded at an end of the fastening protrusion, and the holding portion allows the fastening protrusion to be engaged with the fastening groove, wherein the fastening protrusion and the holding portion are extended in different directions, wherein
the fastening unit comprises:
a body portion comprising the fastening groove and movably coupled with the body unit in a vertical direction;
a pressurizing portion disposed on a top surface of the body portion and, when pushed, moving the body portion into the body unit;
a protruding portion which is disposed on an inner side of the pressurizing portion and protrudes toward the fastening protrusion, wherein the body portion, the pressurizing portion, and the protruding portion are integrally connected;
a guide protrusion extended in a vertical direction; and
an elastic member disposed on the guide protrusion and providing elastic force to the pressurizing portion in the vertical direction, wherein
when the pressurizing portion moves along the vertical direction, an end of the protruding portion pushes an end of the fastening protrusion inserted into the fastening groove outward and the lens unit is separated from the body unit in a horizontal direction as the fastening protrusion is released from the fastening groove according to a movement of the body portion into the body unit in the vertical direction.

2. The goggles of claim 1, wherein a first inclined plane is formed at a part of the fastening protrusion in contact with the protruding portion.

3. The goggles of claim 2, wherein a second inclined plane facing the first inclined plane is formed at a part of the protruding portion in contact with the fastening protrusion.

4. Goggles comprising:
a body unit comprising a pair of fastening units, each of the pair of fastening units comprising a pressurizing portion, a body portion having a fastening groove, and an elastic member; wherein the body portion and the pressurizing portion are integrally connected, wherein the body portion is movable along a vertical direction, and the elastic member provides elastic force to the pressurizing portion in the vertical direction; and a lens unit detachably attached to the body unit and comprising a plurality of fastening protrusions, wherein each of the plurality of fastening protrusions corresponds to each of the pair of fastening units; wherein the fastening groove locks or releases the fastening protrusion, and each of the pair of fastening units is a push button using the elastic member and wherein when the pressurizing portion moves along the vertical direction, an end of the protruding portion pushes an end of the fastening protrusion inserted into the fastening groove outward and the lens unit is separated from the body unit in a horizontal direction, and wherein each of the plurality of fastening protrusions has a holding portion which protrudes in a different direction from a longitudinal direction thereof, and the holding portion allows the fastening protrusion to be engaged with the fastening groove, wherein each of the plurality of fastening protrusions and the holding portion extend in different directions.

5. The goggles of claim 4, wherein the pair of fastening units includes a first fastening unit and a second fastening unit, and the first fastening unit and the second fastening unit are disposed on opposite sides of the body unit.

6. The goggles of claim 5, wherein the first fastening unit has a first pressurizing portion and the second fastening unit has a second pressurizing portion, and wherein when the first pressuring pressurizing portion and the second pressurizing portion are pushed in opposite direction, the lens unit is detached from the body unit.

7. The goggles of claim 4, wherein the body unit includes two pairs of fastening units.

* * * * *